(12) United States Patent
Nishizaka et al.

(10) Patent No.: US 8,203,720 B2
(45) Date of Patent: Jun. 19, 2012

(54) THREE DIMENSIONAL, POSITION OBSERVATION METHOD AND APPARATUS

(75) Inventors: Takayuki Nishizaka, Tokyo (JP); Kana Mizutani, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 748 days.

(21) Appl. No.: 11/988,187

(22) PCT Filed: Jun. 29, 2006

(86) PCT No.: PCT/JP2006/312958
§ 371 (c)(1),
(2), (4) Date: Apr. 2, 2009

(87) PCT Pub. No.: WO2007/004497
PCT Pub. Date: Jan. 11, 2007

(65) Prior Publication Data
US 2009/0219549 A1    Sep. 3, 2009

(30) Foreign Application Priority Data

Jul. 6, 2005 (JP) ................................. 2005-197049

(51) Int. Cl.
*G01B 11/14* (2006.01)
(52) U.S. Cl. ...................... 356/614; 356/620; 356/623
(58) Field of Classification Search .......... 356/614–623
See application file for complete search history.

(56) References Cited

U.S. PATENT DOCUMENTS

| 5,059,022 A * | 10/1991 | Ookawa | 356/124 |
| 2006/0092430 A1 * | 5/2006 | Lizotte | 356/600 |
| 2007/0066871 A1 * | 3/2007 | Yang et al. | 600/173 |

FOREIGN PATENT DOCUMENTS

| JP | 59-129811 | 7/1984 |
| JP | 63-147117 | 6/1988 |
| JP | 2-161332 | 6/1990 |
| JP | 11-513145 | 11/1999 |
| JP | 2000-56233 | 2/2000 |
| JP | 3577514 | 7/2004 |
| JP | 2005-37572 | 2/2005 |
| JP | 3671227 | 4/2005 |

* cited by examiner

*Primary Examiner* — Hoa Pham
(74) *Attorney, Agent, or Firm* — Brinks Hofer Gilson & Lione (57) ABSTRACT

A three-dimensional position observation apparatus provided with a lens system having focusing and diaphragm mechanisms, for forming an image on an imaging plane by light from an observation object includes a beam steering member disposed in a light path extending from the observation object to the imaging plane, for changing a traveling direction of observation light into a plurality of different directions, and an image analyzing unit for analyzing a position of the observation object based on a positional relation between a plurality of images on the imaging plane formed by light passing through the beam steering member.

6 Claims, 11 Drawing Sheets

THREE DIMENSIONAL, POSITION OBSERVATION METHOD AND APPARATUS

RELATED APPLICATIONS

The present application is a 35 U.S.C. §371 national stage filing of International Patent Application No. PCT/JP2006/312958, filed Jun. 29, 2006, to which priority is claimed under 35 U.S.C. §120 and through which priority is claimed under 35 U.S.C. §119 to Japanese Priority Patent Application No. 2005-197049, filed Jul. 6, 2005.

BACKGROUND OF THE INVENTION

1. Field of the Invention

The present invention relates to a three-dimensional position observation method and apparatus for detecting with high precision a three-dimensional position of an observation object, in particular, three-dimensional motion of a microscopic particle under a microscope.

2. Description of the Related Art

In recent years, there has been tremendous progress in optical microscopy, which now reaches a stage where a single protein molecule in an aqueous solution can be studied as an object. This progress has been achieved with the aid of new optical technologies such as total reflection illuminations, development of various types of highly sensitive cameras, improvement in properties of optical filters, and the like. A number of experimental techniques have been developed, and thus a new field called "a single molecular physiology" has emerged.

For example, in a molecular motor or a proteolytic enzyme, substrate binding involves a dynamic structural change, which is considered to be closely linked to a function.

A demanded technique is to make such a structural change occurring inside a single biomolecule visible in a molecular level in a viable condition under a microscope. Innovative techniques from a new perspective are required to advance this growing field to a next new step.

One of techniques for observing a single protein molecule is that a protein is specifically labeled with a fluorescence dye to catch a signal from a single fluorophore.

A fluorescence microscope has a structure incorporating an optical system for emitting an excitation light for brightening the fluorescence dye when receiving a light with a specific wavelength, with use of a dye emitting a light with a longer wavelength than the specific wavelength, and an optical microscope for observing thus generated fluorescence.

Where a reagent bound to a fluorescence dye is bound to a structure inside a cell as an observation object and then the fluorophore is irradiated with a light with a predetermined wavelength, the structure inside the cell as the object generates fluorescence in a black background.

Since the number of fluorophores observable with a general fluorescence microscope is several dozen or more, it is impossible to discern the single fluorophore.

This is because an optical signal strength of a noise, i.e., a background, is greater than that obtained from the single fluorophore.

In this regard, fluorescence microscopes improved for performance upgrade, with which the single fluorophore is visible, have been developed by improving a property of filters, a quality of objective lenses, and the like.

The single fluorophore is observed through the use of such a property of the fluorophore as generating fluorescence by evanescent field illumination.

Specifically, the fluorophore is made to generate fluorescence by illumination of an object sample with use of the evanescent field as a non-propagating light, which is generated around a boundary surface between an aqueous solution containing the object sample and a glass by irradiating the boundary surface with a laser beam at a total reflection angle or greater by means of total reflection from the side of the glass.

Since the evanescent field is exponentially-attenuated with respect to a direction perpendicular to the boundary surface, only a local field near the boundary surface is irradiated, thereby providing the advantage that the intensity of background light is extremely low compared with that of illumination with normal light.

Even under a condition that a number of fluorophores are present in the aqueous solution containing the object sample, there is a low probability that the fluorophore is present on the side of the aqueous solution near the boundary surface, thereby resulting in a low fluorescence from fluorophores other than the single target fluorophore secured to a top of the boundary surface. Therefore, the noise due to the fluorescence from the background light or other fluorophores is extremely low, which enables observation of the fluorescence from the single target fluorophore.

In the single-molecule observation by means of the total reflection, proteins, or biomolecule such as DNA or ATP as a substrate, which are labeled with fluorescence dyes, are bound to a glass surface to detect respective molecules as an independent bright point.

For two-dimensional imaging of a weak signal from the single molecule, a highly sensitive camera is used, such as an image intensifier or a cooled CCD camera.

The present inventors manufactured a total reflection fluorescence microscope to thereby detect a structural change of a specific part of the single biomolecule in real time by observation.

For example, "Total Reflection Fluorescence Microscope" described in Japanese Patent No. 3,577,514 relates to the basic concept and the optical system of this technique and discloses a structure of the total reflection fluorescence microscope which enables observation of a dye molecule having a vibrating surface oriented in an arbitrary direction.

"Total Reflection Type Fluorescence Microscope and Illumination Optical System" described in Japanese Patent No. 3,671,227 by the present inventors discloses a total reflection fluorescence microscope which enables observation of an target dye molecule regardless of a direction of shaking moment of a sample bound to a fluorophore.

As described above, although observation of a single biomolecule has become possible, a positional information obtainable according to the prior art is two-dimensional information. That is, the information on a vertical direction in which an objective lens moves cannot be obtained.

Observation of the three-dimensional positional information of an atomic molecule moving under a microscope achieves quantum leaps such as precise detection of displacement of the single protein molecule.

For example, the following documents also relate to the fluorescence microscope in the prior art: Japanese Patent Application Laid-Open No. 2005-37572, "Illumination Device for Fluorescence Microscope and Fluorescence Microscope"; Japanese Patent Application Laid-Open No. 2000-56233, "Device for Focusing with Adjustments Wavelength or Wavelength Region in Light Irradiation Path in Microscope"; and PCT National Publication No. 11-513145, "Confocal Microscope with Doublet System".

There has been tremendous improvement in optical microscopy such as a bright field microscopy, a dark field microscopy, a phase difference microscopy, a differential interference microscopy, and a laser confocal microscopy. However, the positional information obtained by conventional microscopic observation is two-dimensional information in a surface (an x-y plane) parallel to a slide glass corresponding to a viewing plane, and positional information on a direction (a z-axis) perpendicular to the aforementioned surface cannot be obtained.

SUMMARY OF THE INVENTION

It is an object of the present invention to provide a three-dimensional position observation method and an apparatus for implementing the method, which three-dimensionally detects a position of an observation object simultaneously and also contributes to high precision detection of three-dimensional motion of one protein molecule moving under a microscope.

According to a first aspect of the invention, a three-dimensional position observation method using a three-dimensional position observation apparatus provided with a lens system having focusing and diaphragm mechanisms, for forming an image on an imaging plane by light from an observation object includes disposing a beam steering member in a light path extending from the observation object to the imaging plane, the beam steering member for changing a traveling direction of observation light into a plurality of different directions, and analyzing a position of the observation object based on a positional relation between a plurality of images on the imaging plane formed by light passing through the beam steering member with an image analyzing unit.

According to a second aspect of the invention, a three-dimensional position observation method using a three-dimensional position observation apparatus provided with a lens system having focusing and diaphragm mechanisms, for forming an image on an imaging plane by light from an observation object includes disposing a beam steering member in a light path extending from the observation object to the imaging plane, for changing a part of a traveling direction of observation light, and analyzing a position of the observation object based on a positional relation between an image on the imaging plane formed by light passing through the beam steering member and an image on the imaging plane formed by light not passing through the beam steering member with an image analyzing unit.

According to a third aspect of the invention, a three-dimensional position observation apparatus provided with a lens system having focusing and diaphragm mechanisms, for forming an image on an imaging plane by light from an observation object includes a beam steering member disposed in a light path extending from the observation object to the imaging plane, for changing a traveling direction of observation light into a plurality of different directions, and an image analyzing unit for analyzing a position of the observation object based on a positional relation between a plurality of images on the imaging plane formed by light passing through the beam steering member.

According to a fourth aspect of the invention, a three-dimensional position observation apparatus provided with a lens system having focusing and diaphragm mechanisms, for forming an image on an imaging plane by light from an observation object includes a beam steering member disposed in a light path extending from the observation object to the imaging plane, for changing a part of a traveling direction of observation light, and an image analyzing unit for analyzing a position of the observation object based on a positional relation between an image on the imaging plane formed by light passing through the beam steering member and an image on the imaging plane formed by light not passing through the beam steering member.

It is preferable that the beam steering member be a wedge prism, which contributes to simplification of a structure.

It is preferable that the beam steering member be two wedge prisms each having the same inclination angle, and that the two wedge prisms be disposed in a combined form such that inclination directions of inclination surfaces are reversely oriented. In this manner, the image is easily divided into two.

It is preferable that at least one of the wedge prisms be disposed such that the inclination surface faces a side of the imaging plane, which simplifies structuring of the optical system.

It is preferable that the imaging plane be a light receiving section of an imaging unit such as a video camera, which enhances convenience of an image analyzing process.

It is preferable that the three-dimensional position observation apparatus have a structure of a fluorescence microscope to observe a fluorescence dye.

It is preferable that the observation object be a microscopic particle bound to a fluorescent particle and contained in an aqueous solution to detect with high precision three-dimensional displacement of a protein or the like.

It is preferable that the image analyzing unit calculates a center of brightness of each of the plurality of images on the imaging plane independently to process calculation.

It is preferable that the image analyzing unit determine displacement of the observation object in a direction parallel to the imaging plane based on a displacement amount in the same direction of the plurality of images on the imaging surface.

It is preferable that the image analyzing unit determine displacement of the observation object in a direction perpendicular to the imaging plane based on a displacement amount in an opposite direction of the plurality of images on the imaging surface.

This invention enables detection of three-dimensional displacement of the microscopic particle with the precision of angstrom order in principle, thereby achieving imaging of dynamic features of proteins or the like, which contributes to the elucidation of the operating principle of a molecular motor or a proteolytic enzyme.

DESCRIPTION OF THE PREFERRED EMBODIMENTS

Hereinafter, embodiments of the present invention will be described with reference to drawings.

In examples cited herein, microscopic particles that are bound to fluorophores and contained in an aqueous solution are observed with a fluorescence microscope. However, any means for forming an image of a sample can be employed as a fluorescence microscope having an arbitrary illumination means. The present invention is not limited to a minute object but can be appropriately applied to a large object. As for a minute substance, for example, a microscopic particle of about 10 nm or the single fluorophore is applicable.

Figure 1:
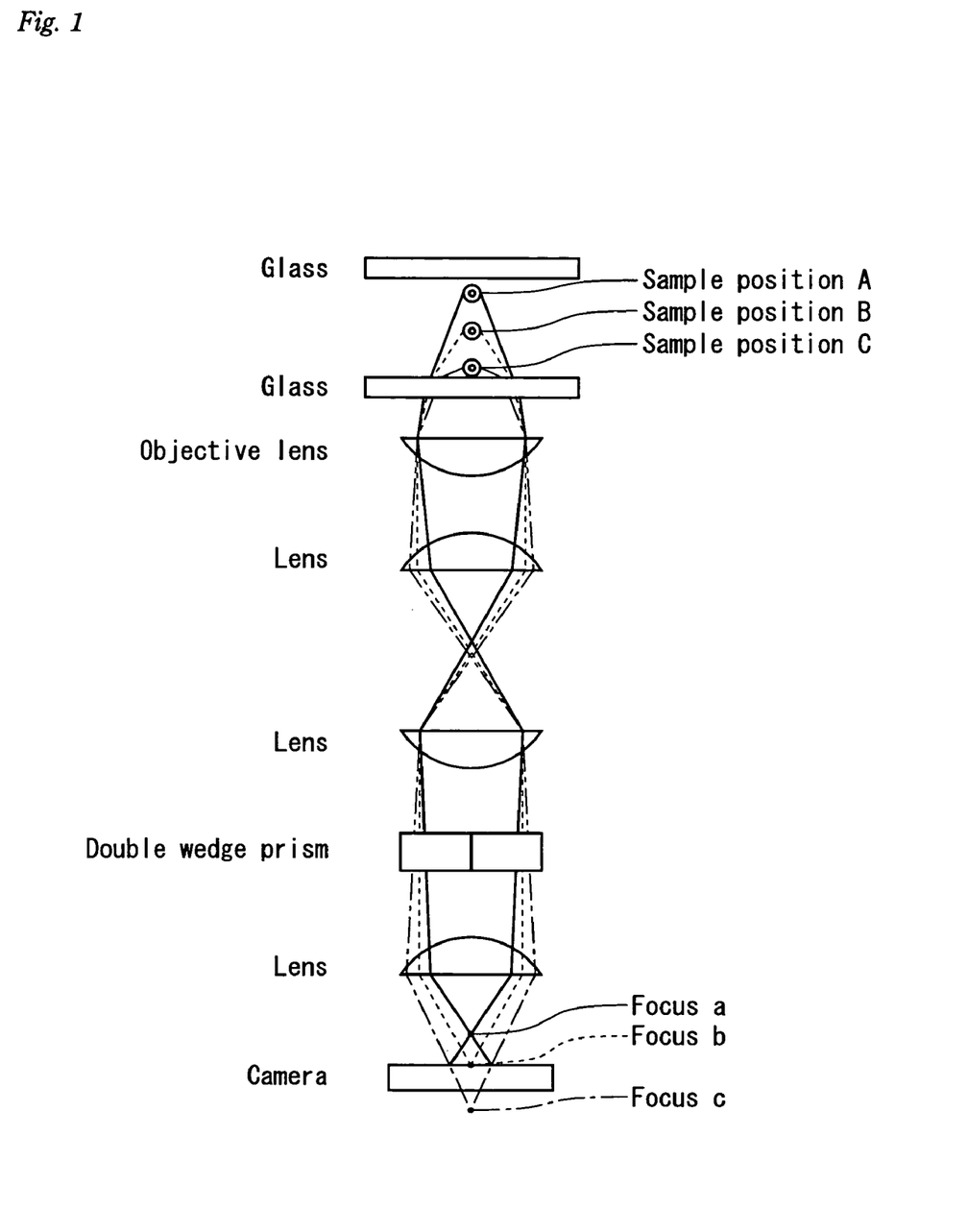
FIG. 1 is a view illustrating an essential structure of an observation apparatus according to an embodiment of the invention.
Figure 2:
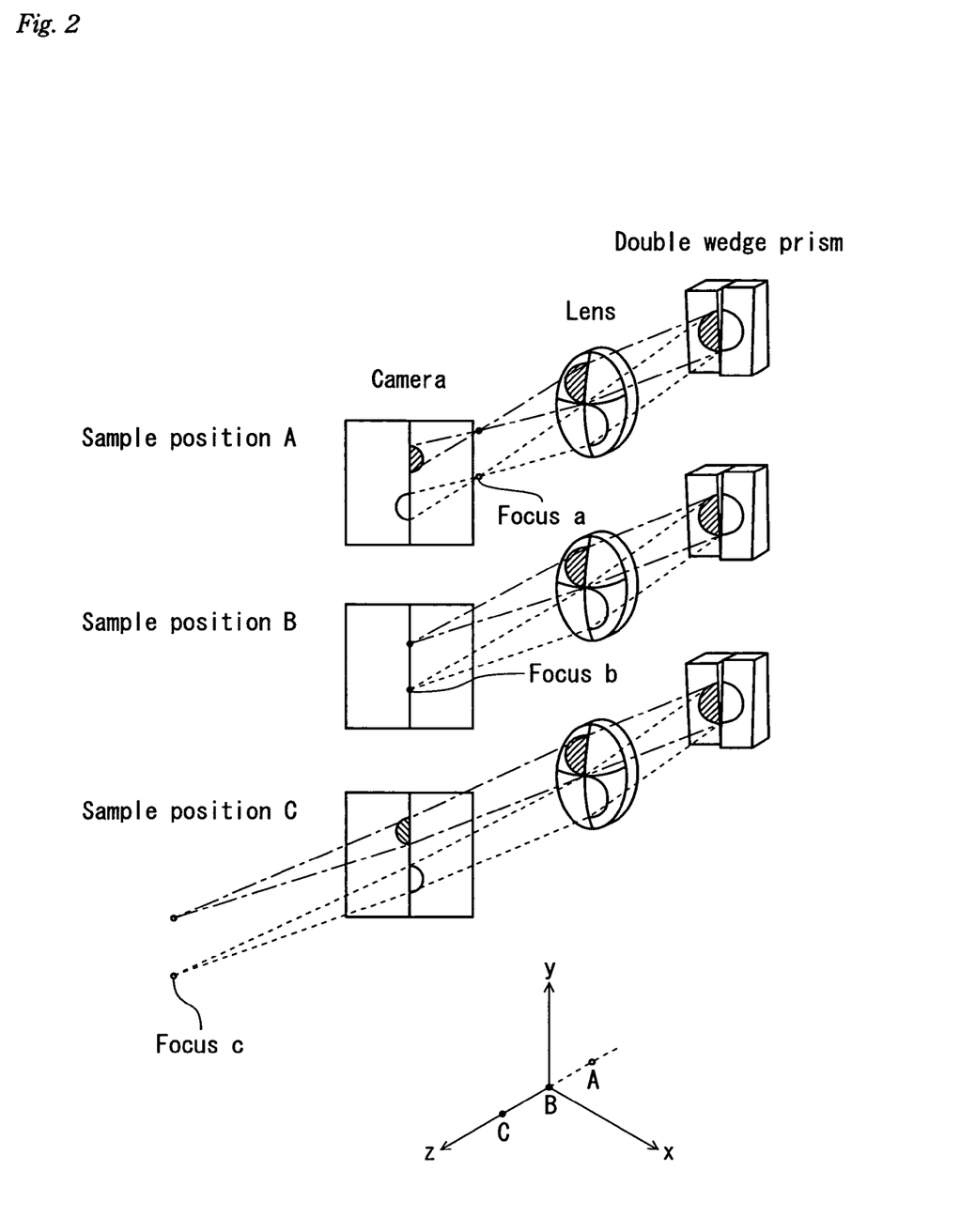
FIG. 2 is a view illustrating an image at the time of displacement of an observation object in a z-direction.
Figure 3:
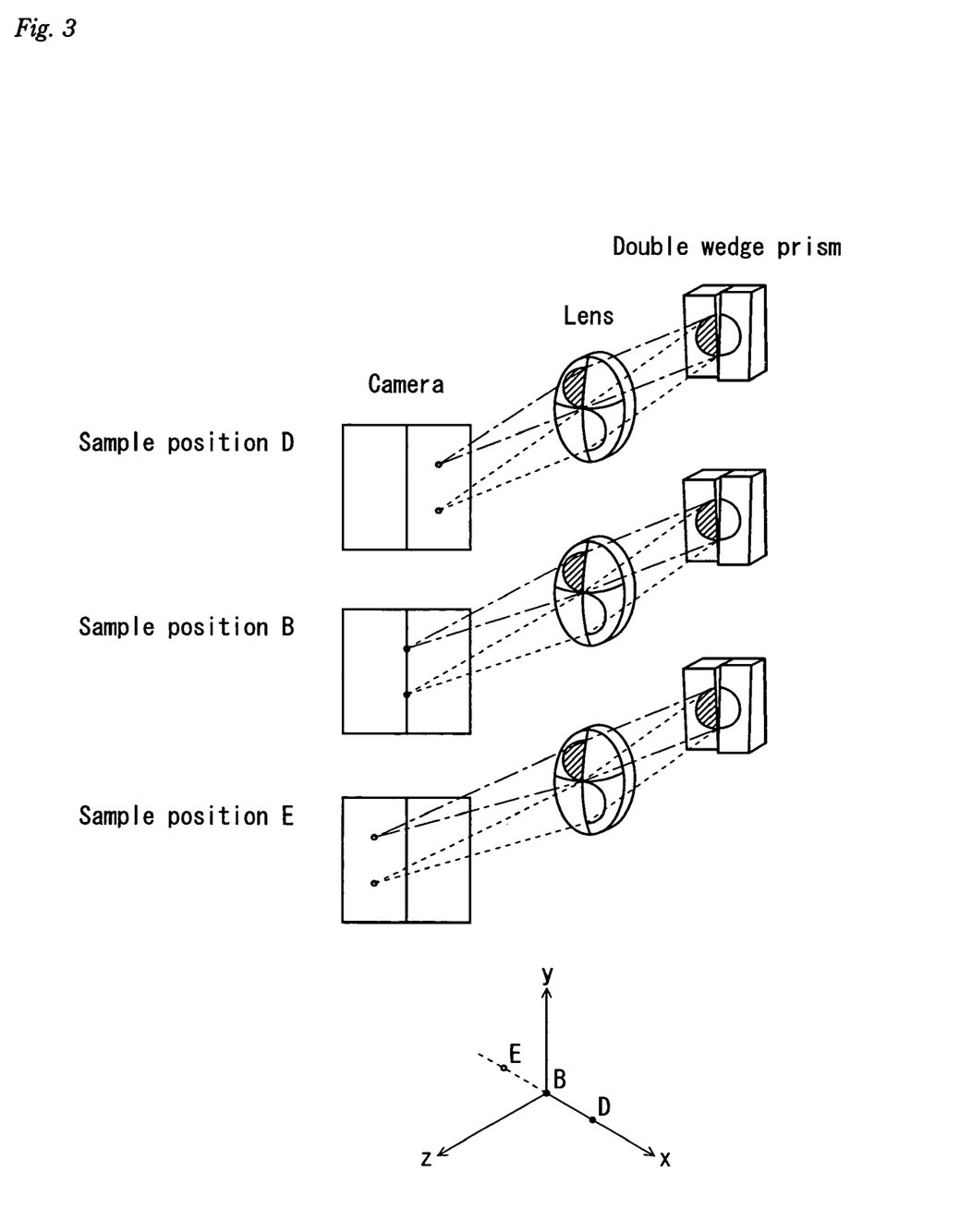
FIG. 3 is a view illustrating an image at the time of displacement of the observation object in an x-direction.
Figure 4:
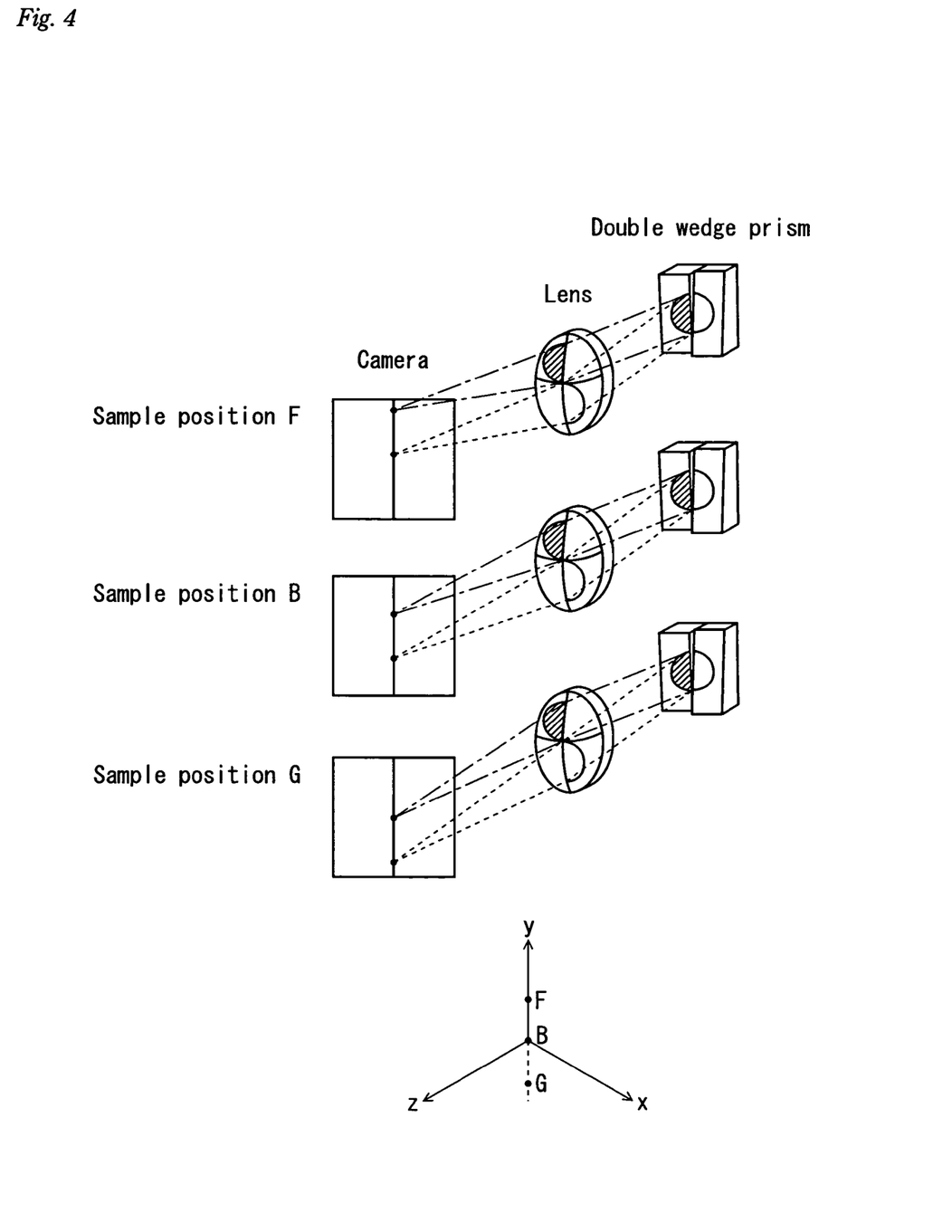
FIG. 4 is a view illustrating an image at the time of displacement of the observation object in a y-direction.

FIG. 1 is a view illustrating an essential structure of an observation apparatus according to an embodiment of the invention. FIGS. 2 to 4 are each a schematic view showing the action of the observation apparatus.

The aqueous solution containing a sample as an observation object having a fluorescence dye is held between a plurality of glass plates.

A beam steering member for changing a traveling direction of observation light into a plurality of different directions is provide in a light path extending from the observation object to an imaging plane of a CCD camera or the like.

A double-wedge prism is employed as the beam steering member in a shown example. Generally, the wedge prism is employed as a useful component for equalizing minor optical path differences.

In the present embodiment, two wedge prisms in the same shape are combined and disposed in a center of the light path. The number of wedge prisms is not limited to two but can be three or more or may be one, as described later. The plurality of wedge prisms are not required to be in the same shape.

The two wedge prisms each having the same inclination angle are used and are disposed in a combined form in a manner that inclination directions of inclination surfaces of the wedge prisms are reversely oriented. It is preferable that the inclination surfaces face the camera.

Since the beam steering member is only required to have the effect of changing the traveling direction of a bright point signal, a mirror or an element which electrically controls a direction of a light ray can be employed instead of the wedge prism.

The observation object is three-dimensionally movable in the aqueous solution. The example shown in FIGS. 1 and 2 shows three sample positions A, B, C in array in a direction of vertical movement of the objective lens (a direction of a z-axis). FIG. 2 schematically shows displacement of two images on the imaging plane when the observation object is displaced in a direction perpendicular to a viewing plane (a z-direction).

Focuses a, b, c correspond to images of the observation object placed at the sample positions A, B, C in the direction of vertical movement of the objective lens (the direction of the z-axis), respectively.

Since each of the wedge prisms changes the traveling direction of the observation light that passes therethrough, the observation light is divided to thereby form two images.

Positions of the focuses a, b, c are displaced in association with the sample positions A, B, C, so that the two images reflect positions and shapes according to the sample positions A, B, C on the imaging plane of the camera.

In this regard, the centers of brightness of the two images on the imaging plane are symmetrically displaced in the opposite direction from each other when the observation object is displaced in the direction perpendicular to the viewing plane.

Thus, displacement in the direction parallel to the viewing plane can be determined as a relative amount from the amount of the displacement.

FIG. 3 is also a view illustrating displacement of two images on the imaging plane when the observation object is displaced in a horizontal direction parallel to the viewing plane (an x-direction).

When the observation object is displaced in the horizontal direction parallel to the viewing plane (corresponding to sample positions B, D, E), the two images on the imaging plane are also displaced in the same horizontal direction.

Thus, displacement in the direction parallel to the viewing plane can be determined as an absolute amount from the amount of the displacement.

In this regard, a position of each image on the imaging plane of a camera is determined by calculating the center of the brightness independently according to an image analysis.

FIG. 4 is a view illustrating displacement of two images on the imaging plane when the observation object is displaced in a vertical direction (a y-direction) parallel to the viewing plane.

In this case also, when the observation object is displaced in a vertical direction parallel to the viewing plane (corresponding to sample positions B, F, G), the two images on the imaging plane are displaced in the same vertical direction in a manner similar to the case described above. Thus, displacement in a direction parallel to the viewing plane can be determined as an absolute amount from the amount of the displacement.

Figure 5:
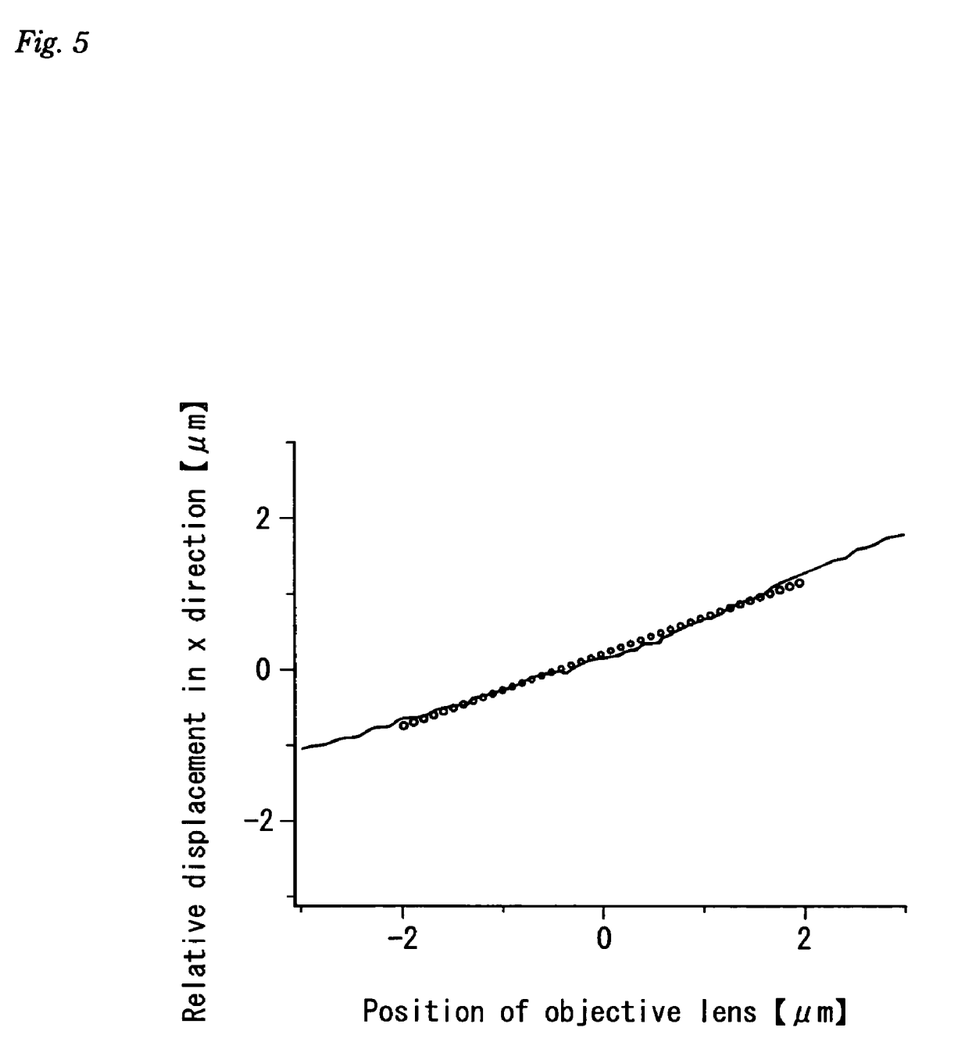
FIG. 5 is a chart showing a relation between displacement in the x-direction and displacement of an objective lens.

FIG. 5 is a chart showing a relation between displacement in the x-direction and displacement of the objective lens. A solid line indicates an example of a typical experimental value while a dotted line indicates an average value.

To determine the absolute amount of displacement in the z-direction, a relation between displacement of the objective lens and displacement in the x-direction was indirectly determined by moving the objective lens up and down.

Specifically, the objective lens was displaced 0.1 μm by 0.1 μm with respect to the fluorescent particle secured to the viewing plane to thereby measure a relative positional change of the two images. As a result, a relation of "relative displacement in the x-direction=0.46×displacement in the z-direction" was determined in this embodiment.

Figure 6:
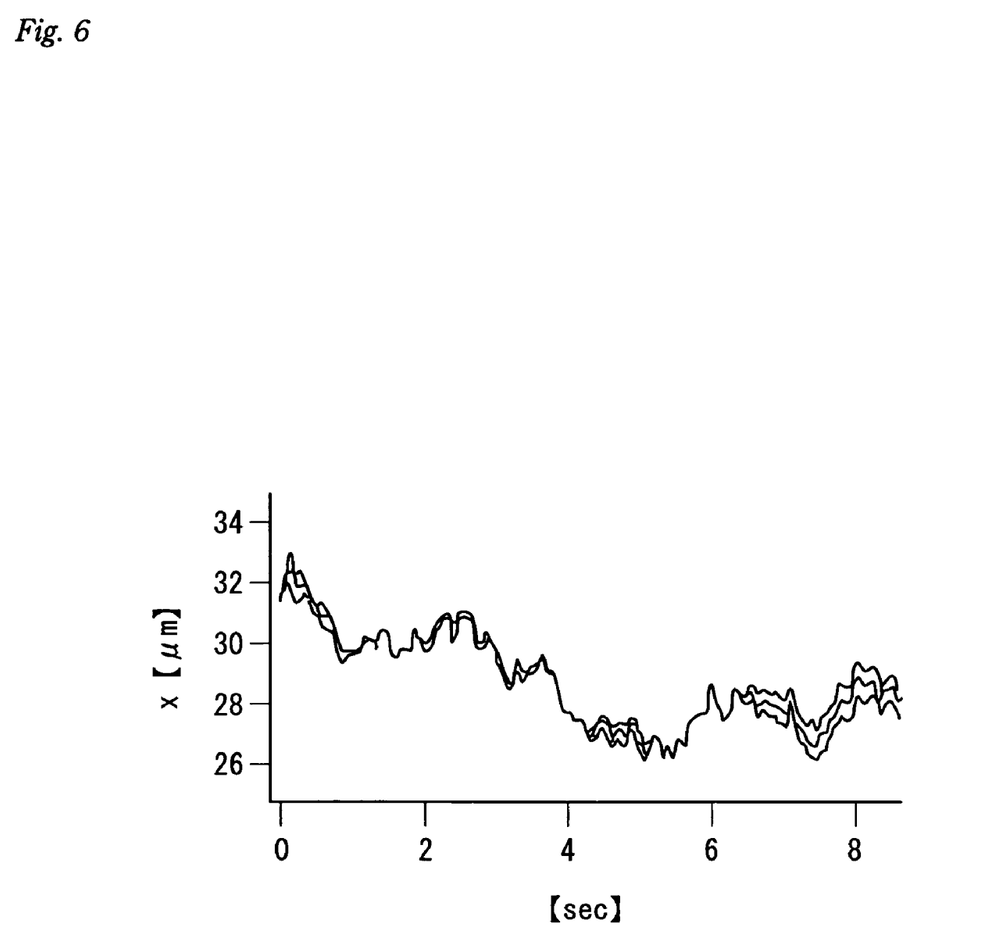
FIG. 6 is a chart showing displacement of a single fluorescent particle in the x-direction over time.
Figure 7:
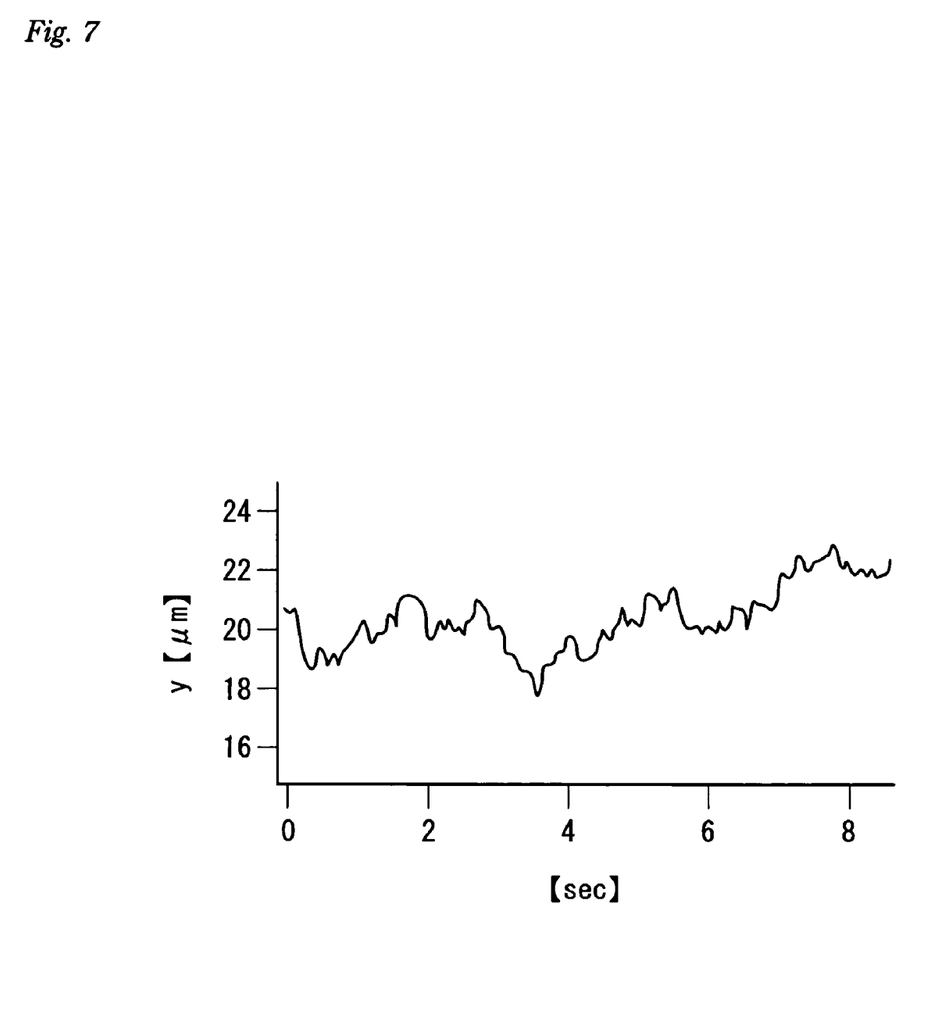
FIG. 7 is a chart showing displacement of the single fluorescent particle in the y-direction over time.
Figure 8:
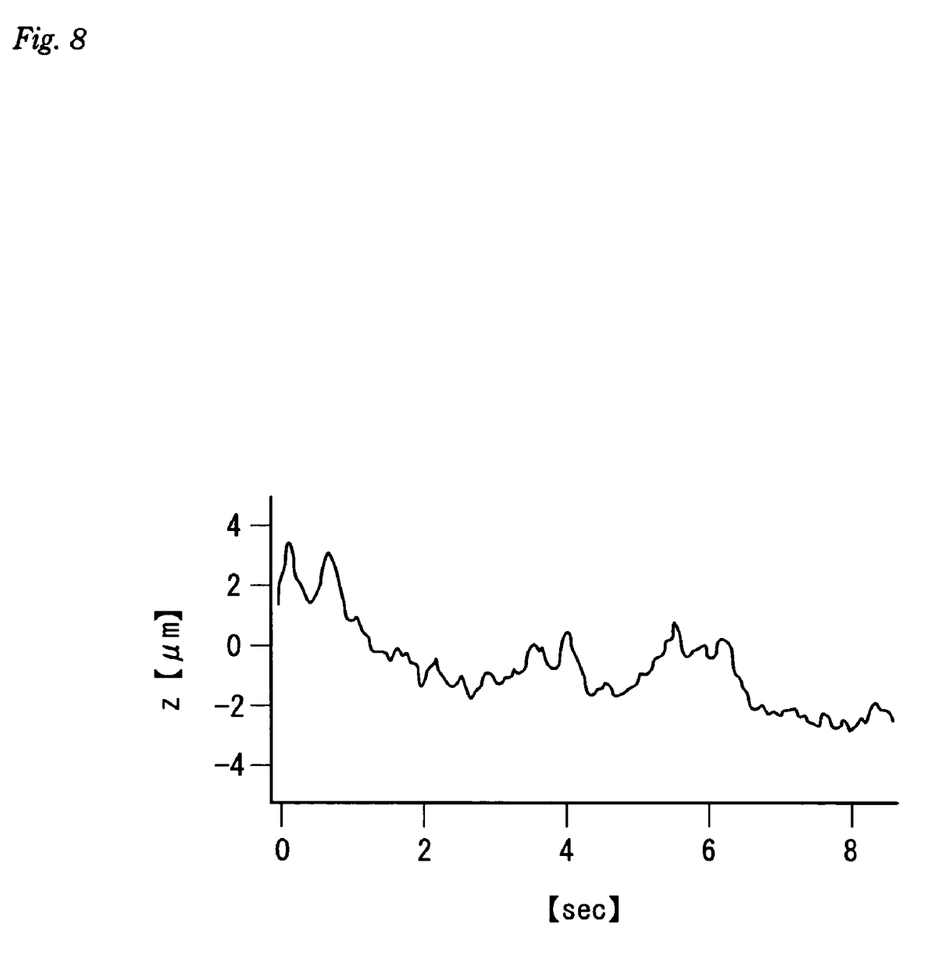
FIG. 8 is a chart showing displacement of the single fluorescent particle in the z-direction over time.
Figure 9:
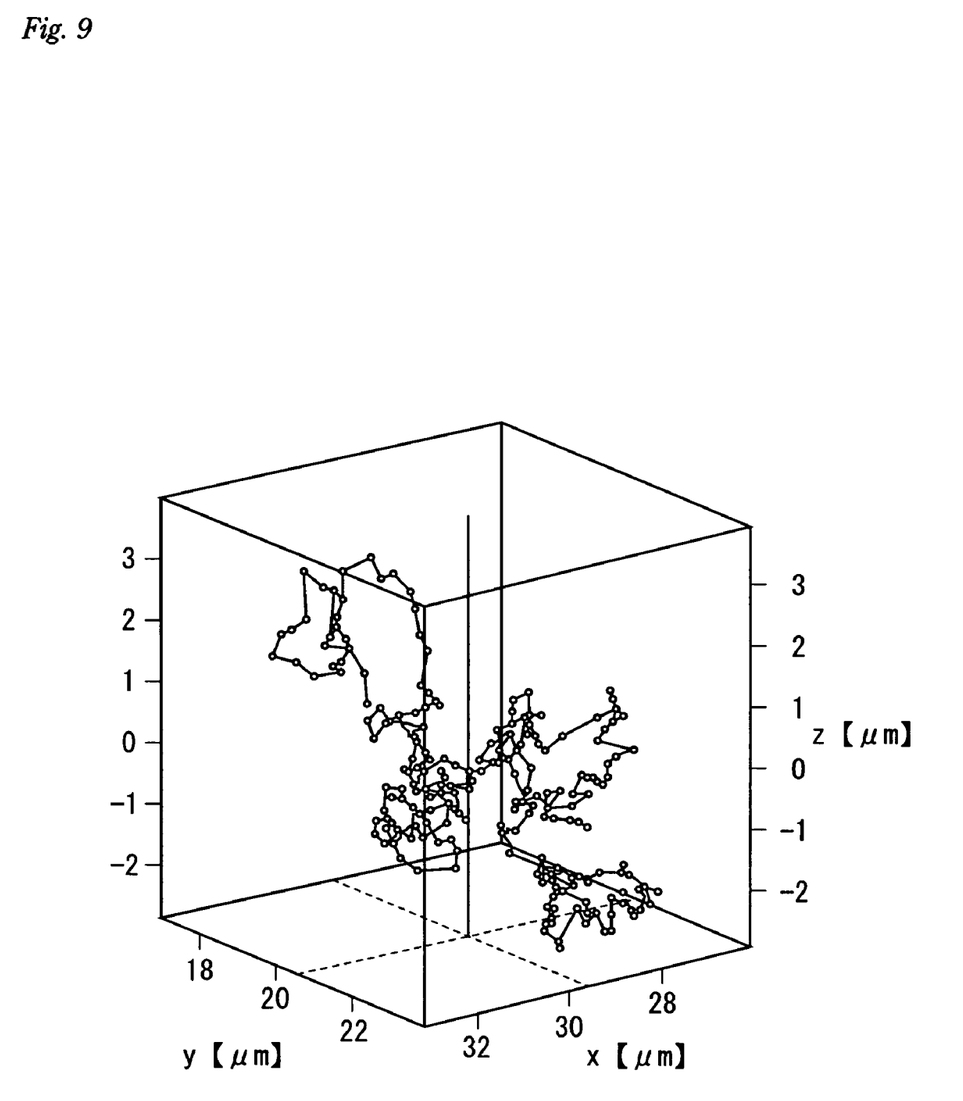
FIG. 9 is a graph showing in three dimensions displacement of the single fluorescent particle over time.

Brownian motion was analyzed utilizing the above system. FIGS. 6, 7, and 8 are charts showing displacement of the single fluorescent particle with a diameter of 0.5 μm for 8 seconds in x, y, and z directions, respectively. FIG. 9 is a graph showing this displacement in three dimensions. Dots in FIG. 9 were plotted every 33 milliseconds.

Thus, a trail of the particle moving under Brownian motion was three-dimensionally detected.

Figure 10:
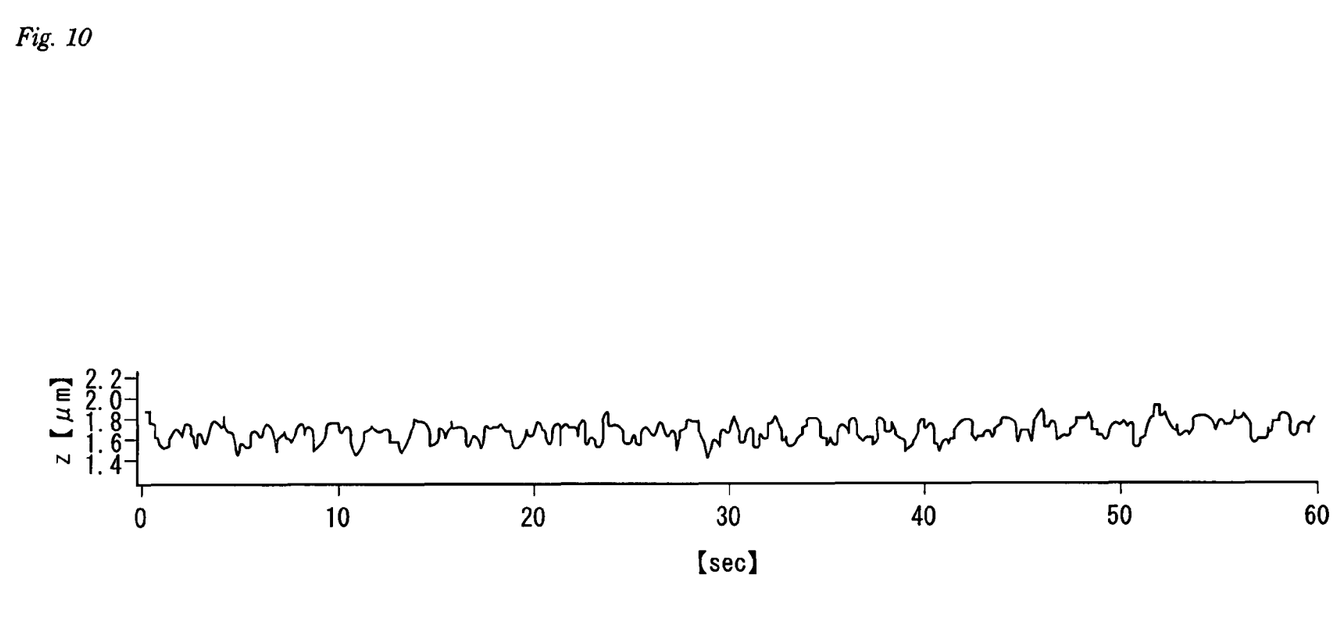
FIG. 10 is a chart showing displacement in the z-direction at the time of rectangular-wave input.
Figure 11:
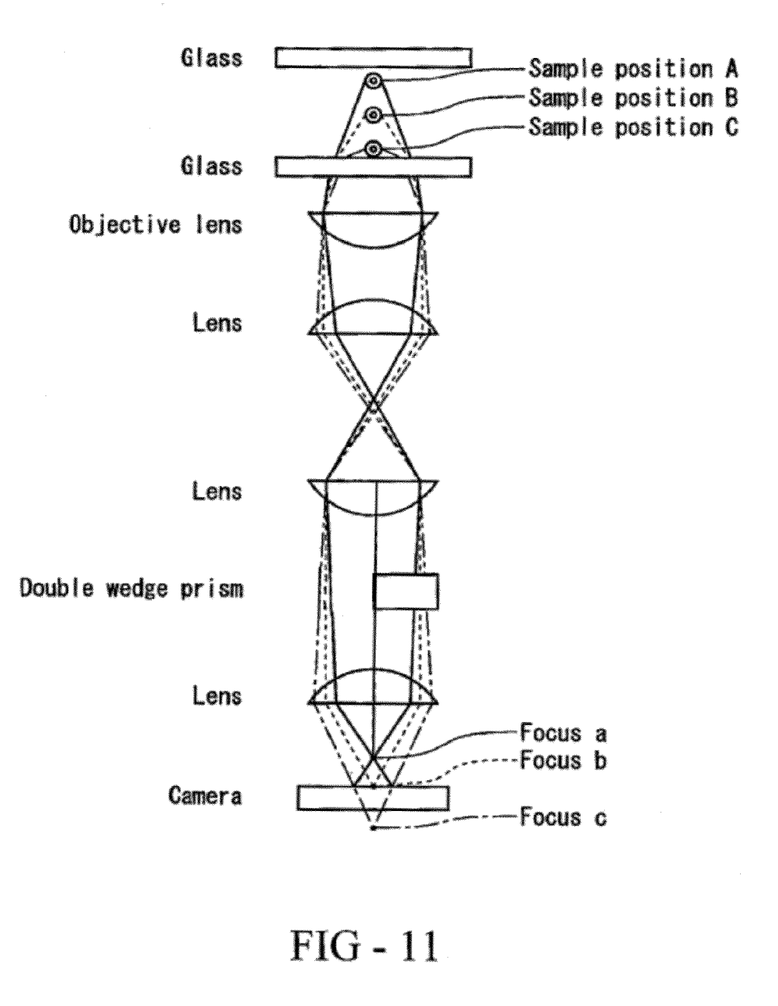

FIG. 10 is a chart showing displacement in the z-direction at the time of input of a rectangular wave with an amplitude of 20 nm and a frequency of 0.5 Hz.

The positional precision of the single fluorescent particle absorbed to a glass surface was determined. The results are a value up to 4 nm in the x-y direction and a value up to 15 nm in the z-direction. This result revealed that the nanometer-order movement in the direction parallel to the viewing plane and 10 nanometer-order movement in the perpendicular direction can be three-dimensionally detected with respect to the single fluorescent particle.

Furthermore, the present invention also has an advantage that the three-dimensional positional information can be obtained from the single formed image.

The positional information with the precision of angstrom order can be obtained by keeping stability of a stage, lengthening exposure time of the single image, and enhancing filtering of the imaging data.

Using a dark-field illumination, the present invention is capable of tracking the position of a 0.5 μm polystyrene bead with ~1 nm accuracy and 1 ms time resolution. Spatial resolution of the system was evaluated from the standard deviation of the position of the sample that was immobilized on the glass surface. For z-direction, a fixed bead showed 1.6 nm deviation for 8 s at 0.125 ms time interval. The accuracy increased by accumulating the captured image sequences; the spatial resolution reached 5.6 Å with 1 ms time intervals, and notably, 1.1 Å with 32 ms.

The present invention is applied to observation of quantum dots. Quantum dots nano crystals (commercially available from Invitrogen Co.) has the size of 5-20 nm. By viewing the Qdot® 605 under a fluorescence microscope with cooled CCD camera, deviation of z-position of quantum dots was estimated to be ~5 nm. This method affords new perspectives on motility observed under microscopes in cell biology and biophysics, such as movement of organelles or proteins in living cells, and tracking of single motor proteins or their substrates labeled with single fluorophores.

It is not necessarily required to form the plurality of wedge prisms as described above. The plurality of wedge prisms may be used, through which not all the observation light passes, but the observation light that travels in a straight line without polarization may be generated.

In this case also, displacement of the two images on the imaging plane can be detected in a manner similar to the case described above. Thus, a position of the observation object can be analyzed based on a positional relation between the image on the imaging plane formed by light passing through the beam steering member and the image on the imaging plane formed by light not passing through the beam steering member.

A difference from the above embodiment is that an optical device is simplified and that a relative distance between the two images on the imaging plane is reduced by half.

The present invention enables the three-dimensional positional information of the observation object to be obtained with a simple structure. The present invention can be applied to any proteins with the aid of a label using the single fluorescent particle, and dynamic behavior of the single molecule can be traced with the precision of angstrom order.

Thus, a structural change of a biomolecule can be displayed in real time in three dimensions, which provides the momentum to the single molecular physiology and can be used for various purposes and is industrially very useful.

The invention claimed is:

1. A three-dimensional position observation apparatus provided with a lens system having focusing and diaphragm mechanisms, for forming an image on an imaging plane by light from an observation object, the three-dimensional position observation apparatus comprising:
    a beam steering member disposed in a light path extending from the observation object to the imaging plane, for changing a part of a traveling direction of observation light; and
    an image analyzing unit for analyzing a position of the observation object based on a positional relation between an image on the imaging plane formed by light passing through the beam steering member and an image on the imaging plane formed by light not passing through the beam steering member.

2. The three-dimensional position observation apparatus according to claim 1, wherein the beam steering member is a wedge prism.

3. The three-dimensional position observation apparatus according to claim 2, wherein the beam steering member is two wedge prisms each having the same inclination angle, and wherein the two wedge prisms are disposed in a combined form such that inclination directions of inclination surfaces are reversely oriented.

4. The three-dimensional position observation apparatus according to claim 3, wherein at least one of the wedge prisms is disposed such that the inclination surface faces a side of the imaging plane.

5. The three-dimensional position observation apparatus according to claim 2, wherein at least one of the wedge prisms is disposed such that the inclination surface faces a side of the imaging plane.

6. A three-dimensional position observation method using a three-dimensional position observation apparatus provided with a lens system having focusing and diaphragm mechanisms, for forming an image on an imaging plane by light from an observation object, the three-dimensional position observation method comprising:
    disposing a beam steering member in a light path extending from the observation object to the imaging plane, for changing a part of a traveling direction of observation light; and analyzing a position of the observation object based on a positional relation between an image on the imaging plane formed by light passing through the beam steering member and an image on the imaging plane formed by light not passing through the beam steering member with an image analyzing unit.

* * * * *